United States Patent [19]

Mizutani et al.

[11] 4,059,006
[45] Nov. 22, 1977

[54] LIQUID QUALITY-EVALUATING APPARATUS

[75] Inventors: Masumi Mizutani, Gifu; Hiromichi Hata; Masasuke Shimazaki, both of Yokohama, all of Japan

[73] Assignees: Showa Industries Co., Ltd., Gifu; Fujisoku Electric Co., Ltd., Kawasaki; Kitoku Co., Ltd., Tokyo, all of Japan

[21] Appl. No.: 751,040

[22] Filed: Dec. 16, 1976

[30] Foreign Application Priority Data

Dec. 22, 1975 Japan ............................ 50-171939[U]
Dec. 22, 1975 Japan ............................ 50-171940[U]

[51] Int. Cl.² ............................................. G01N 25/08
[52] U.S. Cl. .................................................. 73/17 A
[58] Field of Search ............... 73/17 A, 61.3; 340/236

[56] References Cited

U.S. PATENT DOCUMENTS

| | | | |
|---|---|---|---|
| 3,621,706 | 11/1971 | Markey | 73/17 |
| 3,780,565 | 12/1973 | Hawkins | 73/17 |
| 3,844,159 | 10/1974 | Mizutani et al. | 73/17 |

Primary Examiner—Herbert Goldstein
Attorney, Agent, or Firm—Flynn & Frishauf

[57] ABSTRACT

A liquid quality-evaluating apparatus for liquids whose boiling point or vapor lock point vary by deterioration includes a heating vessel made of heat conductive and electrically conductive material and adapted to hold a brake fluid whose quality is to be determined. The heating vessel has an opening which is closed by an electrically and heat insulating removable cover and the wall of the heating vessel near the bottom is fitted with a nozzle acting as a siphon. The cover carries a hollow cylindrical electrode so disposed as to slightly dip into a brake fluid received in the vessel. A heat-responsive resistance element for detecting the temperature of the brake fluid is received in the hollow cylindrical electrode. A heater is provided below the heating vessel to heat the brake fluid received therein. A current cutoff-detecting circuit is electrically connected between the heating vessel and the hollow cylindrical electrode. A liquid temperature-indicating circuit for displaying the temperature of the brake fluid is connected to the heat-responsive resistance element. A liquid temperature-indicating pointer used with the liquid temperature-indicating circuit is locked by an output signal from the current cutoff-detecting circuit which is actuated when the level of the brake fluid falls when the brake fluid boils.

9 Claims, 5 Drawing Figures

LIQUID QUALITY-EVALUATING APPARATUS

This invention relates to improvements in a quality-evaluating apparatus for liquids, for example, motor vehicle brake fluid.

A liquid whose quality should be determined includes various types, for example, a motor vehicle brake fluid. Motor vehicles are often run at a high speed and consequently a motor vehicle brake apparatus tends to generate a considerable amount of heat, leading to the frequent occurrence of a so-called vapor lock. This vapor lock arises when a brake fluid is heated approximately to a boiling pint or vapor lock point, where it is necessary continuously to apply a strong braking force. This is known to considerably decrease the braking force of a motor vehicle. The vapor lock is regarded as a source of serious danger, because the resultant lowered braking force of a motor vehicle is likely to give rise to traffic accidents. A brake fluid should have a high boiling point to prevent the vapor lock. The recent tendency is toward application of a high boiling point fluid in order to elevate the braking applying property of a motor vehicle.

The higher the boiling point or the vapor lock point of a brake fluid, the more noticeable to the decline in its boiling point or the vapor lock point caused by its bygroscopic property. Where the brake fluid is highly heated and pressurized during a braking operation, with resultant decomposition, then low-boiling ingredients are grown, thereby lowering the vapor lock point. Therefore, a brake fluid is deteriorated by absorption of atmospheric moisture. Where a brake fluid is used particularly in highly humid air, an increased water content in the brake fluid leads to lower its boiling point, with the higher possibility of giving rise to vapor lock. For prevention of this undesirable event, it is necessary periodically to examine the water and low-boiling ingredients content of a brake fluid, thereby determining its quality.

The vapor lock point is the initial boiling point of the brake fluid and means a lower temperature than the boiling point thereof. Generally, a brake fluid 4 is a mixture of different liquid materials, and consequently has a different boiling point and vapor lock point. To prevent a vapor lock occurring at the vapor lock point, it is important to measure said vapor lock point in particular.

The present inventors have already developed a liquid quality-evaluating apparatus which can determine the quality of a brake fluid easily and quickly. This liquid quality evaluating apparatus is already disclosed in the following literature filed by the same applicant as that of the present patent application.

A patent application P2305 586.9 filed in West Germany on Feb. 5, 1973; and U.S. Pat. No. 3,844,159 issued on Oct. 29, 1974.

The liquid quality-evaluating apparatus already disclosed is roughly intended to electrically detect whether a brake fluid whose quality is to be determined has a temperature higher or lower than a prescribed level. However, this liquid quality-evaluating apparatus has been found to be accompanied with various problems, though capable of quickly and easily determining a liquid quality.

The first problem was that the previous liquid quality-evaluating apparatuss did not always correctly judge the quality of a brake fluid. The reason is that vapor lock does not arise when a brake fluid is heated to a boiling point but when the initial boiling point or vapor lock point is reached. However, the previous apparatus measured the boiling point of a brake fluid after it is presented a sudden blow, possibly giving rise to errors in judging the quality of the brake fluid. The previous apparatus never failed to be provided with first and second vessels. When a brake fluid began to be shifted from the first to the second vessel by a sudden blow, measurement was made of the boiling point of the brake fluid. The actually measured boiling point of the brake fluid was determined to be higher than that of the brake fluid initially placed in the first heating vessel for measurement. The above-mentioned event was to the fact that the brake fluid whose boiling point was actually measured contained a smaller amount of not only water but also low-boiling ingredients due to heating. The reason is that the water and low-boiling ingredients contained in the nonmeasured brake fluid initially received in the first heating vessel were progressively evaporated by heating before a sudden blow, and consequently the brake fluid had a lower water and low-boiling ingredients content than when held in the first heating vessel.

The second problem with the previous liquid quality-evaluating apparatus was that said apparatus tended to make an erroneous measurement. The reason is that a needle-like electrode was provided for the second vessel; untimely of deposition of a small amount of brake fluid on said electrode led to electrical conduction between said electrode and second vessel before the brake fluid was fully transferred from the first to the second vessel; and said untimely electrical conduction caused the temperature of the brake fluid to be measured to appear as if the temperature denoted the boiling point of the brake fluid. Further, a small amount of brake fluid sometimes leaked from the first to the second vessel, when the first vessel happened to be shaken, the brake fluid received in the first vessel was unduly heated, though not to a boiling point, or an unnecessarily larger amount of brake fluid was received in the first vessel. Moreover, the needle-like electrode was soiled by deposition of dust or any other foreign matter. All those events also led to the erroneous measurement of the boiling point of a brake fluid.

It is accordingly a first object of this invention to provide a liquid quality-evaluating apparatus capable of correctly determining the quality of any liquid.

A second object of the invention is to provide a liquid quality-evaluating apparatus adapted to carry out a reliable temperature-measuring operation free from errors.

SUMMARY OF THE INVENTION

To attain these objects, this invention provides a liquid quality-evaluating apparatus for determining the boiling point or vapor lock point of a liquid varying in its deterioration, which comprises a vessel formed of heat-conductive and electrically conductive material and having an opening to receive a prescribed amount of sample liquid whose boiling point is to be measured; discharge siphon, one end of which is disposed at the bottom of the vessel to communicate with the liquid in the vessel and the other end of which lies outside of the vessel; a removable cover made of heat-insulating material to substantially airtightly close the opening of the vessel; heating means for heating the vessel and the liquid in the vessel; an electrode, one end of which lies is removably received in the vessel for contact with the liquid whose boiling point is to be determined and the other end of which is fixed to the removable cover; a current cutoff-detecting circuit comprising at least the electrode, the vessel and the liquid received therein to form a closed electrical circuit and producing an output signal when the liquid ceases to contact the electrode; means for detecting the temperature of the liquid received in the vessel and for generating electrical signals which correspond to the detected temperature; and display means for indicating upon receipt of the electrical signals whether the sample liquid has a boiling point higher or lower than a reference temperature.

DETAILED DESCRIPTION

Let us now explain in detail by reference to the accompanying drawings the preferred embodiments of a liquid quality-evaluating apparatus in connection with, by way of example but not as limitation on the scope of this invention, a motor vehicle brake fluid to be evaluated.

Figure 1:
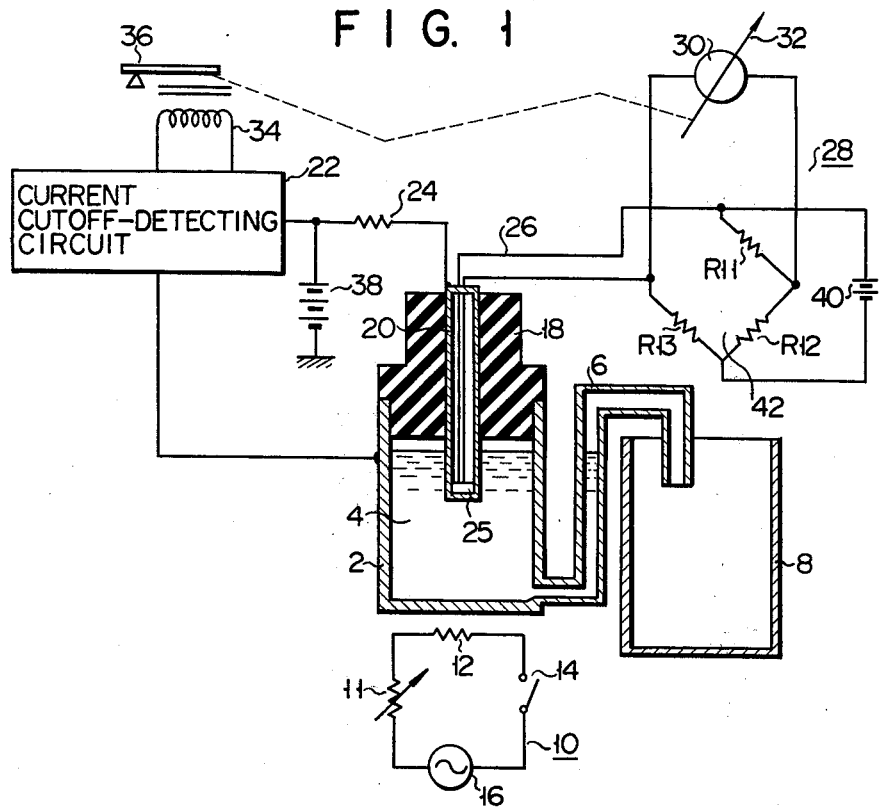
FIG. 1 is a schematic block diagram of a liquid quality-evaluating apparatus according to one embodiment of this invention.

FIG. 1 showing a liquid quality-evaluating apparatus according to an embodiment of this invention illustrates a heating vessel 2 of about 0.5 to 0.6 c.c. for holding a liquid. This heating vessel 2 is formed of heat-conductive and electrically conductive material and is provided at the top with an opening about 10 mm in diameter through which to pour, for example, a motor vehicle brake fluid 4 whose boiling point is to be measured. One end of an approximately U-shaped nozzle 6 about 2 mm in inner diameter is connected to the wall of the heating vessel 2 near the bottom for communication with the inner bottom portion thereof. The nozzle 6 extends to a higher position than the level of about 0.5 to 0.6 c.c. of brake fluid 4. The other end of the nozzle 6 is directed downward to form a siphon for drawing off a brake fluid 4 from the heating vessel 2. As used herein, the term "siphon" is defined to mean a U-shaped or V-shaped transfer tube used first to lift a brake fluid 4 and then let it fall, namely, to remove the brake fluid 4 from the vessel 2, when pressure is applied to said fluid 4. The other end of the nozzle 6 enters a discharged liquid receptacle 8 for receiving brake fluid 4 drawn off from the heating vessel 2. However, this discharged liquid receptacle 8 is not always required for the object of this invention. Namely, it is possible to extend the nozzle 6 outside of the liquid quality-evaluating apparatus for removal of a discharged brake fluid 4.

A heat source 10 is provided below the heating vessel 2. The heat source 10 is formed of a closed circuit comprising a variable resistor 11, heater 12 switch 14 and power source 16 and is designated quickly to heat a brake fluid 4 to a temperature of about 100° to 300° C. The opening of the heating vessel 2 is sealed with a cover 18 to form a sealed vessel after the brake fluid 4 is poured into the heating vessel 2. The cover 18 is made of heat-insulating material, and contains a hollow cylindrical electrode 20. The hollow cylindrical electrode 20 projects from the cover 18 into the heating vessel 2 sufficiently downward so as to dip the electrode at 20 to a predetermined depth into the brake fluid 4 filled in the heating vessel 2. The electrode 20 is not limited to the hollow cylindrical form, but may take a needle form shown in FIG. 4. The point is that the electrode 20 should be fitted to the cover 18 so as not to break the airtightness provided by the cover 18 and heating vessel 2. A current cutoff-detecting circuit 22 is connected through a resistor 24 between the hollow cylindrical electrode 20 and heating vessel 2 made of electrically conductive material. The arrangement of the current cutoff-detecting circuit 22 will later be described by reference to FIG. 3. This current cutoff-detecting circuit 22 detects whether the heating vessel 2 is filled with a prescribed amount of brake fluid 4 whose boiling point is to be measured. This current cutoff-detecting circuit 22, electrode 20, brake fluid 4 and heating vessel 2 collectively constitute a closed circuit. When an interspace between the electrode 20 and heating vessel 2 is rendered nonconducting due to the fall of the level of the brake fluid 4, then the current cutoff-detecting circuit 22 generates an output signal denoting said current cutoff. A temperature-detecting element 25 such as a heat-responsive resistance element which detects the temperature of the brake fluid 4 received in the heating vessel 2 when heated by the heat source 10 is provided on the inner bottom plane of the hollow cylindrical electrode 20. This heat-responsive resistance element 25 formed of, for example, a thermistor is connected to a liquid temperature-detecting circuit 28 by means of a lead 26 which is covered with electrically insulating material and extends through the hollow portion of the cylindrical electrode 20 and along the outside of the heating vessel 2.

Figure 2:
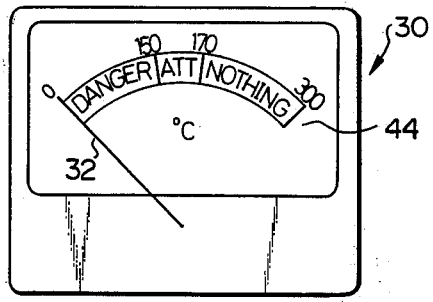
FIG. 2 is an enlarged front view of a dial of a temperature-indicator of FIG. 1.

A thermometer 30 included in the liquid temperature-detecting circuit 28 indicates, as shown in FIG. 2, the temperature of a brake fluid 4 detected by the heat-responsive resistance element 25 by means of a pointer on a temperature scale. The thermometer 30 is designed as to hold a pointer 32 in place when the current cutoff detecting circuit 22 issues a signal denoting current cutoff. When an exciting coil 34 is operated by a signal denoting current cutoff which has been delivered from the current cutoff detecting circuit 22, the pointer 32 is immovably locked by a movable iron strip 36 of the exciting coil 34.

There will now be described by reference to FIG. 3 a concrete arrangement of the current cutoff-detecting circuit 22. This circuit 22 is of the Darlington type including a transistor TR1 whose base is connected to the heating vessel 2 through a resistor R1 and whose collector is connected to the plus terminal of a D.C. source 38 through a resistor R2 and a transistor TR2 whose base is connected to the collector of the transistor TR1 and whose collector is connected to the plus terminal of the D.C. source 38 through the exciting coil 34. The emitters of both transistors TR1, TR2 are grounded, and the collectors thereof are connected to the resistor 24 and then to the hollow cylindrical electrode 20 through the resistor R2 or the exciting coil 34. As previously described, the current cutoff-detecting circuit 22 issues a signal denoting current cutoff when an interspace between the heating vessel 2 and hollow cylindrical electrode 20 is rendered nonconducting. While current is supplied to the base of the transistor TR1 from the D.C. source 38 through the hollow cylindrical electrode 20, brake fluid 4 and heating vessel 2, the current cutoff-detecting circuit 22 does not generate a signal denoting current cutoff. Where, however, the level of the brake fluid 4 in the heating vessel 2 sufficiently falls to render an interspace between the heating vessel 2 and hollow cylindrical electrode 20 nonconducting, then the current cutoff-detecting circuit 22 produces a signal showing current cutoff. When current ceases to flow through the base of transistor TR1 to render it nonconducting, then D.C. voltage is impressed on the base of the transistor TR2 from the D.C. source 38. Accordingly, the transistor TR2 is operated to allow direct current to pass through the exciting coil 34. Namely, a signal denoting current cutoff is supplied to said exciting coil 34.

There will now be described a concrete arrangement of the liquid temperature-detecting circuit 28. This circuit 28 comprises the heat-responsive element 25, resistors R11, R12, R13, bridge circuit 42 between both input terminals of which a D.C. source 10 is connected, and a thermometer 30 formed of an ordinary D.C. galvanometer, for example, of a movable solenoid type connected between the output terminals of the bridge circuit 42. As is known, the liquid temperature-detecting circuit 28 indicates the temperature of the brake fluid 4 by converting changes in the resistance of the heat-responsive resistance element 25 which depend on the temperature of the brake fluid 4 into the angle through which the pointer 32 of the thermometer 30 is deflected. As already mentioned, when a signal denoting current cutoff is supplied to the exciting coil 34, the pointer 32 of the thermometer 30 is locked by the movable iron strip 36. The thermometer has a temperature scale (FIG. 2) graduated from 0° to 300° C. The temperature scale 44 is divided into three indication regions showing those temperature ranges of 0° to 150° C, 150° to 170° C and 170° to 300° C, respectively. The three regions are marked with characters of "DANGER" in red, "ATT" in yellow, and "NOTHING" in green, respectively. The character "DANGER" denotes that the brake fluid whose boiling point has been measured is already so deteriorated as to require replacement with a fresh batch of braking fluid. The character "ATT" shows that the brake fluid whose boiling point has been determined is falling in quality and calls for attention. The character "NOTHING" proves that the brake fluid whose boiling point has been checked still has a satisfactory quality.

A liquid quality-evaluating apparatus according to one embodiment of this invention evaluates the quality of, for example, a brake fluid 4 by the following process.

The cover 18 of the heating vessel 2 is taken off the opening. About 0.5 to 0.6 c.c. of brake fluid 4 is poured into the heating vessel 2. The opening of the heating vessel 2 is closed by the cover 18. The hollow cylindrical electrode 20 is slightly dipped into the brake fluid 4 received in the heating vessel 2 in airtightness. Since, at this time, electrical conduction takes place between the heating vessel 2 and electrode 20, the current cutoff-detecting circuit 22 is not put into operation. Therefore, the thermometer 30 indicates the current temperature of the brake fluid which has been measured by the temperature detecting 25.

Where the switch 14 of the heat source 10 is closed, the heating vessel is heated by the heater 12. As a result, the temperature of the brake fluid 4 received in the heating vessel 20 rapidly increases. In about a few seconds, the brake fluid 4 boils. As previously described, the boiling point of the brake fluid 4 varies with the water and low-boiling ingredients content. A high quality brake fluid containing less than 3% of water and a small amount of low-boiling ingredients boils at temperature of about 160° to 200° C.

There will now be described the process by which the brake fluid 4 heated by the heater 12 of the heat source 10 finally presents a sudden blow. First, gases dissolved in the brake fluid 4 are expanded and bubble up through the brake fluid 4. Then there occurs the evaporation of water and low-boiling ingredients which have a lower boiling point than the brake fluid 4 and which are already absorbed thereto. Finally when drawn near to the boiling point, the brake fluid 4 itself volatilizes with an increasing amount of bubbles and last presents a sudden blow. Increased pressure in the airtight vessel constituted by the heating vessel 2 and cover 18 due to the presence of air, steam, vapor of the low-boiling ingredients and brake fluid bubbles causes the level of the brake fluid 4 gradually to fall. As a result, the brake fluid 4 is transferred little by little from the heating vessel 2 to the discharged liquid receptacle 8, through the nozzle 6. Later, the blowing brake fluid 4 is rapidly brought into said receptacle 8 through the nozzle 6.

While the brake fluid 4 is initially shifted from the heating vessel 2 to the discharged liquid receptacle 8, electrical conductivity is established between the hollow cylindrical electrode 20 and heating vessel 2 due to the dip ring of said electrode 2 in the brake fluid 4. Later when the level of the brake fluid 4 drops due to pressure in the heating vessel 2 being increased by the evaporation of water and low boiling ingredients contained in the brake fluid 4 and the subsequent evaporation of said fluid itself 4 with occurrence of bubbles thereof, then the hollow cylindrical electrode 20 ceases to contact the brake fluid 4, obstructing electrical conduction between the electrode 20 and heating vessel 20. At this time, the current cutoff-detecting circuit 22 is put into operation. An output signal from said circuit 22 locks the pointer 32 of the thermometer 30 which has already been noticeably deflected due to the increased heating of the brake fluid 4. The graduation on the temperature scale 44 at which the pointer 32 is now locked determines whether the brake fluid tested has a good quality. The pointer 32 of the thermometer 30 is not locked at the sudden blow or outrush of the brake fluid 4 but when it just begins to boil, thereby correctly evaluating the quality of the brake fluid 4.

With a mixture of liquid materials such as a brake fluid 4, the vapor lock point can be measured very accurately. The vapor lock point or initial boiling point of a single fluid coincides with its boiling point. Therefore, measurement is only made of the boiling point.

There will now be described by reference to FIGS. 4 and 5 a liquid a liquid quality-evaluating apparatus according to another embodiment of this invention.

The difference between the second embodiment and the first one is that the hollow cylindrical electrode 20 is replaced by a needle-like electrode 120; a heat-responsive resistance element 125 is fitted to the heating vessel 2, instead of being received in the hollow cylindrical electrode 20; and the liquid temperature detecting circuit 28 of the first embodiment is substituted by a lamp-display type. Except in the above-mentioned respects, the second embodiment of FIG. 4 has substantially the same fundamental arrangement as the first embodiment of FIG. 1. Therefore, the parts of FIGS. 4 and 5 which are the same as those of FIG. 1 are denoted by the same numerals, description thereof being omitted.

Figure 4:
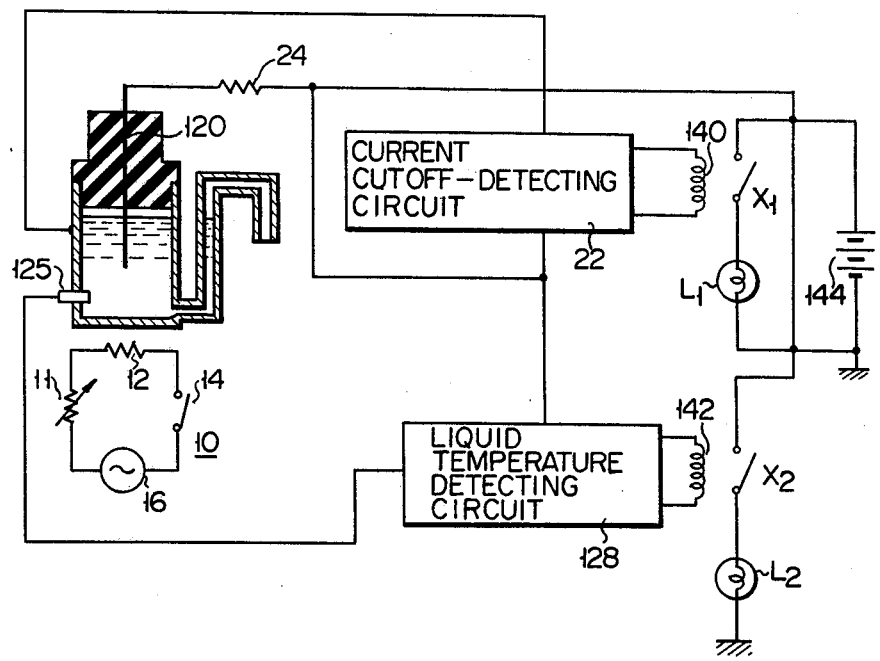
FIG. 4 is a schematic block diagram of a liquid quality-evaluating apparatus according to another embodiment of the invention.

The second embodiment of FIG. 4 in which the needle-like electrode 120 is provided and the heat-responsive resistance element 125 is fitted to the heating vessel 2 presents substantially the same effect as the first embodiment of FIG. 1. However, the first embodiment of FIG. 1 can more correctly detect the temperature of a liquid than the second embodiment of FIG. 4, because the heat-responsive resistance element 25 is positioned substantially in the brake fluid 4.

There will now be described a concrete arrangement of the second embodiment of FIG. 4 and its operation of displaying the quality of the brake fluid 4.

Figure 3:
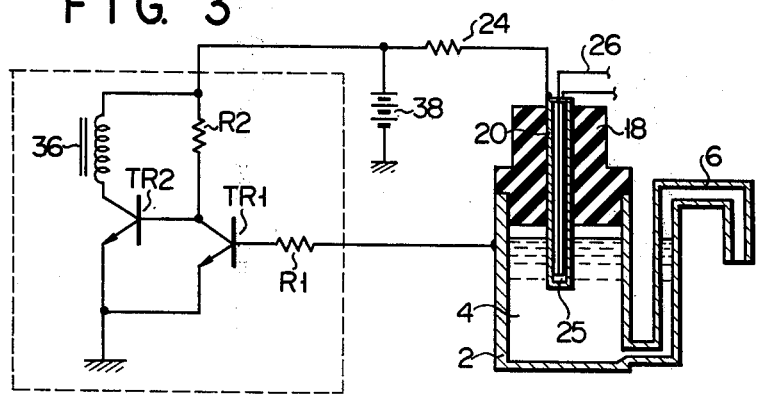
FIG. 3 shows a concrete arrangement of a current cutoff-detecting circuit of FIG. 1.

Referring to FIG. 4, the output terminal of the current cutoff-detecting circuit 22 having the same arrangement as shown in FIG. 3 is provided with an exciting coil 140 for controlling the operation of a first normally open contact $X_1$. The output terminal of the liquid temperature detecting circuit 128 is fitted with an exciting coil 142 for controlling the operation of a second normally open contact $X_2$. A lamp $L_1$ is connected in series to the exciting coil 140, and a lamp $L_2$ is connected in series to the exciting coil 142. A series circuit including the exciting coil 140 and lamp $L_1$, and a sereies circuit including the exciting coil 142 and the lamp $L_2$ are connected between a plus terminal of a D.C. source 144 and ground.

Figure 5:
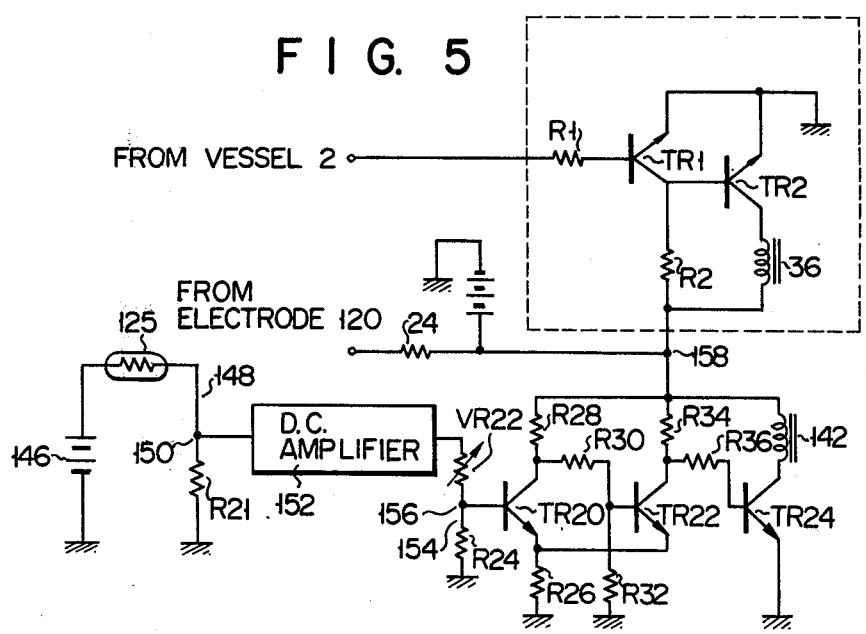
FIG. 5 is a concrete diagram of a liquid temperature-detecting circuit of FIG. 4.

Referring to FIG. 5 showing a concrete arrangement of the liquid temperature-detecting circuit 128, the liquid temperature-detecting circuit 128 comprises a variable current path 148 formed of a series circuit including the heat-responsive resistance element 125 connected between ground and a positive pole of a D.C. source 146 whose negative pole is grounded; a series circuit 154 including the resistor R24 and a variable resistor VR22 connected through a D.C. amplifier 152 between the ground and a common junction 150 of a resistor 21 and the heat-responsive resistance element 125 of said variable current path 148; a Schmidt circuit including a transistor TR20 whose base is connected to a junction 156 of the resistor 24 and the variable resistor VR22 of the series circuit 154, whose emitter is grounded through a resistor R26 and whose collector is connected through a resistor R28 to a positive terminal 158 of the D.C. source 144, a transistor TR22 whose emitter is connected to the emitter of the transistor TR205 whose base is connected through a resistor R30 to the collector of the transistor TR20 and also grounded through a resistor R32 and whose collector is connected through a resistor R34 to a positive output terminal 158; and a driver circuit including a transistor TR24 whose base is connected through a resistor R36 to the collector of the transistor TR22, whose emitter is directly grounded, and whose collector is connected through the exciting coil 142 to the terminal 158 of the liquid temperature-detecting circuit 128. An amount of current supplied from the D.C. source 146 to the variable current path 148 varies with the resistance of the heat-responsive resistance element 125, leading to a change in a level of voltage which appears across both ends of the resistor R21 of the variable current path 148 and is impressed on a D.C. amplifier 152. The threshold voltage of the Schmidt circuit is preset at a level denoting a boiling point of the brake fluid 4, for example, 150° C which represents a border line between the good and bad qualities of the brake fluid 4 by adjusting the resistance of the variable resistor VR22 of the series circuit 154.

Where, with the second embodiment of FIG. 4, the current cutoff-detecting circuit 22 is operated ahead of the liquid temperature-detecting circuit 128, then the first normal open contact $X_1$ is closed earlier than the second open contact $X_2$ to cause the first lamp $L_1$ to be lighted before the second lamp $L_2$, thus proving that the brake fluid 4 whose boiling point has been measured is already deteriorated. Conversely, where the liquid temperature-detecting circuit 128 is actuated ahead of the current cutoff-detecting circuit 22, then the second normally open contact $X_2$ is closed earlier than the first normally open contact $X_1$ to cause the second lamp $L_2$ to be lighted before the first lamp $L_1$, thus showing that the brake fluid 4 whose boiling point has been determined has a good quality.

As previously described, the liquid quality-evaluating apparatus of this invention measures the boiling point or vapor lock point of the brake fluid 4 just when it begins to boil, thereby evaluating the brake fluid 4 very correctly. Further, since said measurement is carried out only when the electrode ceases to have an electrical contact with the brake fluid 4, the liquid quality evaluating apparatus of the invention is reliably operated without errors resulting from the soiling of, for example, the electrode. Should low electrical conduction arise between the electrode and heating vessel due to, for example, the electrode being soiled, the electrode which is fitted to the cover can be easily cleaned. Moreover, the embodiment of this invention in which the heat-responsive resistance element is provided in the heating vessel determines the temperature of the brake fluid more correctly than has been possible in the past.

The liquid quality-evaluating apparatus is applicable not only to a motor vehicle brake fluid but also any other liquid whose boiling point or impurity content is to be determined.

What we claim is:

1. A liquid quality-evaluating apparatus for determining the boiling point or vapor lock point of a liquid, comprising:
   a vessel made of heat-conductive and electrically conductive material and having an opening to receive a prescribed amount of a sample liquid whose boiling point or vapor lock point is to be determined;
   a discharge siphon, one end of which is disposed at the bottom of the vessel for communication with the liquid in the vessel and the other end of which extends outside of the vessel, for removing the liquid from the vessel after its quality has been evaluated;
   a removable cover made of heat-insulating material to substantially airtightly close the opening of the vessel;
   heating means for heating the vessel and the liquid in the vessel;
   an electrode, one end of which is removably received in the vessel for contact with the sample liquid whose boiling point is to be determined and the other end of which is fixed to the removable cover;
   a current cutoff-detecting circuit including at least the electrode, the vessel and the sample liquid received in the vessel to form a closed electrical circuit and adapted to issue an output signal when the sample liquid ceases to contact the electrode, thereby detecting a predetermined level of the liquid in the vessel;

means for detecting the temperature of the sample liquid in the vessel and for generating electrical signals corresponding to the detected temperature; and display means coupled to the temperature detecting means for indicating in response to said electrical signals whether the sample liquid in the vessel has a higher or lower boiling point than a reference temperature.

2. A liquid quality-evaluating apparatus according to claim 1, wherein the electrode is a hollow cylindrical electrode; and the means for detecting the temperature of the sample liquid includes a heat-responsive resistance element located on the inner bottom surface of the hollow cylindrical electrode.

3. A liquid quality-evaluating apparatus according to claim 1, wherein the electrode is a needle-like electrode.

4. A liquid quality-evaluating apparatus according to claim 1, wherein the means for detecting the temperature of the sample liquid includes a heat-responsive resistance element mounted to the vessel.

5. A liquid quality-evaluating apparatus according to claim 1, wherein the heating means includes a variable resistor and an electrically-resistive heating element connected in series with the variable resistor to an electrical power source.

6. A liquid quality-evaluating apparatus according to claim 1, wherein the current cutoff-detecting circuit includes an active circuit element provided with input and output electrodes, the vessel, the sample liquid in the vessel, the electrode, a first D.C. power source, and an exciting coil; the input electrode of the active circuit element being connected to the first D.C. power source through the sample liquid in the vessel and electrode; the output electrode of the active circuit element being connected to the first D.C. power source through the exciting coil; the means for detecting the temperature of the sample liquid comprises a liquid temperature-detecting circuit including a bridge circuit, one arm of which constiutes the heat-responsive resistance element received in the vessel and a second D.C. source connected between a pair of terminals of the bridge circuit; and the temperature-indicating means includes a temperature-indicating D.C. galvanometer connected between the other pair of terminals of the bridge circuit and means for locking a pointer of the galvanometer in response to energization of the exciting coil.

7. A liquid quality-evaluating apparatus according to claim 1, wherein the current cutoff-detecting circuit includes an active circuit element provided with input and output electrodes, the vessel, the sample liquid in the vessel, the electrode, a first D.C. power source and an exciting coil; the input electrode of the active circuit element being connected to the first D.C. power source through the vessel, sample liquid and electrode; the output electrode of the active circuit element being connected to the first D.C. power source through the exciting coil; the means for detecting the temperature of the sample liquid comprises a liquid temperature-detecting circuit including a variable current path formedd of a series circuit including a second D.C. power source, a heat-responsive resistance element received in the vessel and a resistor, a D.C. amplifier whose input terminal is connected to the series circuit lying between the heat-responsive element and the resistor, a Schmidt circuit connected to the output terminal of the D.C. amplifier and impressed with a threshold voltage denoting the boiling point of the sample liquid representing a boundary between the good and bad qualities thereof, a drive circuit whose input terminal is connected to the output terminal of the Schmidt circuit, and a second exciting coil connected between the driver circuit and the first D.C. power source; and the display means includes a first normally open lamp circuit which is closed when the second exciting coil is energized and a second normally open lamp circuit which is closed when the first exciting coil is actuated.

8. A liquid quality-evaluating apparatus according to claim 1, wherein said means for detecting the temperature of the sample liquid includes a heat-responsive resistance element coupled to the cover and extending into the vessel.

9. A liquid quality-evaluating apparatus according to claim 1, wherein said cover is made of an electrically insulating and heat insulating material.

* * * * *